US00PP20241P3

(12) United States Plant Patent
Carruth

(10) Patent No.: US PP20,241 P3
(45) Date of Patent: Sep. 1, 2009

(54) CLIMBING MINIATURE ROSE PLANT NAMED 'WEKWAPUNK'

(50) Latin Name: *Rosa hybrida*
Varietal Denomination: WEKwapunk

(75) Inventor: Thomas Carruth, Altadena, CA (US)

(73) Assignee: Greenheart Farms, Inc., Arroyo Grande, CA (US)

( * ) Notice: Subject to any disclaimer, the term of this patent is extended or adjusted under 35 U.S.C. 154(b) by 56 days.

(21) Appl. No.: 11/998,968

(22) Filed: Dec. 3, 2007

(65) Prior Publication Data

US 2009/0144864 P1 Jun. 4, 2009

(51) Int. Cl.
*A01H 5/00* (2006.01)

(52) U.S. Cl. ..... Plt./116

(58) Field of Classification Search ..... Plt./116, Plt./109

See application file for complete search history.

*Primary Examiner*—Annette H Para

(57) ABSTRACT

'WEKwapunk' is a new variety of miniature rose plant with informal, semi-double blossoms of a unique muted russet and smoky lavender with orange centers. Having a columnar and spreading habit makes it suitable for decorative use in a garden or as a specimen plant. This new variety has an above average degree of resistance to powdery mildew and rust.

1 Drawing Sheet

This new invention relates to a new and distinct variety of Miniature Rose Plant. Roses from this same breeding program that bare some resemblance to this new invention are 'WEKroalt' (U.S. Plant Pat. No. 11,518) and 'WEKbecfoj' (U.S. Plant Pat. No. 18,033). All have flowers with relatively few petals, similarly shaped broad petals, and similar irregular arrangement of those petals. All have an upright columnar and spreading growth habit. 'WEKroalt' bares semi-double flowers (about 8 to 12 petals) of striped and flecked red and white coloration. 'WEKbecfoj' bears single-petaled flowers (about 5 to 7 petals) of pastel pink and yellow-striped and flecked coloration. This new invention has semi-double flowers (about 9 to 15 petals) with no striping and is a blend of russet and oranges with a flushing of purples. This new invention and 'WEKroalt' are third generation descendents of MACel' (non-patent) and 'WEKbecfoj' is fourth generation, being a descendent of 'WEKroalt'.

This new invention may also be compared to 'WEKpaltlez' (U.S. Plant Pat. No. 15,155), also from this breeding program. Flowers of 'WEKpaltlez' have similar appearance, color wise, to those of this new invention. Both have a blend and flushing of colors to appear in the Greyed-Purple Group of The Royal Horticultural Society Colour Chart. 'WEKpaltlez' is a larger floribunda rose with plant habit and larger flowers having more petals than this new invention. 'WEKpaltlez' is first generation descendent of 'HARwelcome' (U.S. Plant Pat. No. 6,161). This new invention is second generation descendent of 'HARwelcome'.

Genus and species: *Rosa hybrida.*

Varietal denomination: 'WEKwapunk'.

BACKGROUND OF THE INVENTION

This present invention relates to a new and distinct variety of miniature rose plant. It was created in a greenhouse in Upland, Calif. by crossing the variety known as 'CHEwpeachdell' (U.S. Pat. No. 15,287) as seed parent with 'HARflow' (U.S. Plant Pat. No. 10,478) as pollen parent. Upon recognition of the attributes of this plant within the progeny of the stated cross, it was elected for further testing and observation. Upon recognition that this plant was novel and expressed numerous superior and desirable traits as described below, the plant of this application was assigned an international recognition name of 'WEKwapunk'.

Comparison with Parents:

Its seed parent, 'CHEwpeachdell', is a shrub rose with a very upright to almost columnar growing habit of 5½- to 8½-feet in height, with very vigorous growth and double flowers of peach coloration measuring about 1¾- to 2¼-inches in diameter. Foliage is dark green and semi-glossy.

'HARflow', the pollen parent, is a larger-flowered floribunda with a height of about 3½- to 4¼-feet, producing double flowers of a golden yellow coloration, 3¾- to 4¼-inches in diameter. Foliage is medium green, and very glossy This new invention has the upright and columnar growing habit, the dark green foliage and the flower size, all similar to its seed parent. Both of its parents have double flowers and this new invention has semi-double flowers, usually having fewer than half as many petals as either parent. While they all have a similar quantity of prickles, the prickles of 'WEKwapunk' are a lighter coloration than those of 'CHEwpeachdell' and a darker coloration than the prickles of 'HARflow'. The flowers on this new invention are a unique blend of russet and orange with a flushing of purples.

SUMMARY OF THE INVENTION

Among the features that distinguish this new variety from other presently available rose cultivars of which we are aware is its unique flower color. Other distinguishing characteristics are the arrangement of its petals, its columnar and spreading growing habit, the coloring of its prickles, and its above average disease resistance. This new invention is a rose suitable for decorative use in a garden or as a specimen plant.

Asexual reproduction of the new variety by cuttings as performed in Upland and Arroyo Grande, Calif., shows that the foregoing and other distinguishing characteristics continually come true to form. This new invention is easy to reproduce from softwood cuttings, taking 4 to 8 days to initiate root development under controlled greenhouse conditions.

BRIEF DESCRIPTION OF THE DRAWING

The accompanying photograph illustrates the new variety and shows the flowering thereof from bud to full bloom depicted in color as nearly correct as it is possible to make in a color illustration of the character. Throughout this specification, color references and/or values are based upon The Royal Horticultural Society Colour Chart except where common terms of color definition are employed.

DETAILED BOTANICAL DESCRIPTION

The following description is of 1- to 1½-year-old rose plants of this new variety grown in 3½-inch plastic pots, in a soil-less mix of peat moss and coconut bark, grown outdoors in Arroyo Grande, Calif. in the month of October. Phenotypic expression may vary with environmental, cultural and climatic conditions, as well as differences in conditions of light and soil.

Flowers:

*Blooming habit.*—'WEKwapunk' blooms in flushes throughout the growing season. Flowers are mostly borne singly but are also borne in small clusters of 2 to 5.

PEDUNCLES are about 1 1/16-to 1⅛-inches in length with a caliper of about 3/32-inch and usually straight unless curved upward from a trailing branch. The surface is glossy but with a moderate amount of soft prickles and occasional hairs. The color is near 144A, a medium yellow-green. There is often one or a pair of three-leaflet leaves at the base of the peduncle, where it attaches to the stem.

RECEPTACLES are urceolate, with a glossy surface of a medium yellow-green, between 144A and 146A. There is a smattering of fine, short appressed hairs on the surface. The diameter is about ¼-inch with a height of about 5/16-inch. The top of the receptacle has a diameter of 9/32-inch. The top surface is glossy and glabrous, with a light yellow-green color of near 154C. There is a fine ring about 2/64-inch wide, of a Chrome Yellow near 15C-D, along the outer edge where the stamens are attached. Just inside this ring is another ring, about 3/64-inch wide of near 12C, Aureolin.

After the petals drop, the top surface of the receptacle and the portion of the sepals then exposed to the sun become flushed with near 181A.

*Bud.*—Before the calyx breaks, the bud is about 7/16- to 8/16-inch in length and 11/32- to 12/32-inch in diameter at the widest point. The form is ovate with a truncate base. Bud color is a very dark green, between 146A and 147A, with no anthocyanin coloration and is semi-glossy. There are stipitate glands and hairs on the outer two sepals, concentrated near the base. Sepals extend beyond the tip of the bud by about 9/32-inch.

SEPALS are about 23/32- to 24/32-inch long and about 8/32- to 9/32-inch wide at the widest point. They are ovate with an ovoid base. The apex of the two outermost sepals is acuminate and of the three innermost sepals is acicular. The outer sepals have one or two acuminate foliar appendages along each margin. The inside surface of all sepals is pubescent and a color near 2C and near 191A near the margins. The color of the outside surfaces is near 144C and the outermost sepals are a darker yellow-green, between 146A and 147A, along the margins while that same area along the margins of the three innermost sepals is a little lighter than that, between 144A and 146B. The color of the abaxial surface of the foliar appendages on the outermost sepals is noticeably a darker green, near 137A. The sepals roll back ahead of the petals to a position tight against the peduncle and remain that way until the peduncle drops or as the hip forms.

BLOOM size when fully expanded is 1⅓- to 2-inches in diameter and ¾-inch deep. Petalage count ranges from 9 to 15 with 3 to 7 petaloids, irregularly arranged. Bloom form is with a flattened convex upper profile and the lower profile progresses from flattened convex to flattened concave. Fragrance is slight. From the time the sepals first separate until the petals drop is about 8 days.

PETALS are thick with very good substance. The upper surfaces are velvety and under surfaces are satiny. The shape of the outer petals is oblate and the inner petals are broad fan-shaped. The outer margins of all petals are crescent shaped. The apex is apiculate, sometimes with a small rounded notch on one or both sides of the tip. The arrangement of the petals is over-lapping, not evenly spaced, and there may be more petals and petaloids on one side of the bloom than the other. Length of the outermost petals is about 27/32-inch and the width is about 1-inch.

COLOR observed when the sepals first divide is a deep red, near 45A. During the first few days the basal area of the upper sides of the petals is a red-orange, between 32A and 33A. The remainder of the petals is very heavily flushed with near 187A-B, from the Greyed-Purple Group, giving the appearance of between 183A and 176A, a smoky-russet, and near 183D along the outer edges. The point of attachment is a medium yellow, between 9A and 2A. The underside of the outer petals appears between 183C and 177B, with a basal area of near 35A, Brick Red, and darker, near 34A, along the margins. Where these colors blend together in the middle of the under-surface the color is near 169A, a deep grayed-orange. The point of attachment is a Dresden Yellow, near 5C.

Color of the inner petals is the same as the outer petals except the upper surface is a little darker. The reverse of the inner petals is a little lighter, near 177C, with the basal area of between 34B and 35B and the point of blending near 168A. The reverse of the inner petals may have a streak of a Mimosa Yellow, near 8D, straight from the base to the apex, or streaking of 8D on either side of the middle vein. The point of attachment is still near 5C After a few days the flower is usually full open and colors have lightened. The upper surface of the outer petals appears between 186C and 185C, a muted mauve. The basal area has become between 39A and 41C, a muted medium-red. The point of attachment is near 5C. The basal area of the underside of the petals is near 48B, a muted, deep pink. The remainder of the petal appears near 177A-B which may be the result of a purple near 83A-B flushing over the near 48B. The point of attachment is near 5D Color as the flower ages continues to fade except at the point of attachment. From a distance the flowers appear shades of muted russet and smoky lavender throughout its flowering season. Closer observations reveal flowers of a muted russet washed with purple having vivid orange centers and yellow stamens, as well as older flowers of a smoky lavender and less vivid orange centers. Petals start to drop cleanly form the receptacle after eight days.

PETALOIDS may be deeply cleft; or only half a petal, and with an oblique base, often with anthodium along the main vein when the vein is along one side of the petaloid. Width varies from 8/32- to 25/32-inch at the widest point. The length averages between 25/32- and 26/32-inch but unusually may be only 5/32-inch wide and 9/32-inch long. The color is the same as that of the inner petals, with the exception of any streaking along one side being near 29B, Carrot Red, on the upper surface and near 19D, Egyptian Buff, on the reverse in newly opened flowers. These colors also fade as the bloom ages.

Reproductive organs:

ANDROECIUM are regularly arranged along the outer edge of the top of the receptacle. The color of the top of the receptacle where the stamens is attached is near 15C-D, Chrome Yellow. The quantity of stamens was found to be about 84. The color of the anthers is between 163B and 22C, a grayed, yellow-orange. The color of the pollen sacs along the edges of each anther is near 24A, Tangerine Orange. Filaments are between 1/8- and 1/4-inch, with the longer ones being aligned furthest from the pistils. The color of the filaments is a medium red, near 53D.

GYNOCEIUM are bunched in the center of the receptacle. The quantity varies between two-fifths and one-half as many as the number of stamens. Styles are straight and of medium thickness. The most common length was found to be 4/32-inch but some were 5/32-inch long. The color of the styles is near 53A, Cardinal Red. The color of the stigmas is a medium pink, near 56B. No HIPS were observed.

Foliage:

Pinnately compound leaves are usually comprised of five- and seven-leaflet leaves, and usually with three-leaflet leaves near the base and tip of each stem. Leaflets are shaped moderately ovate to somewhat oval with moderately acuminate apices and rounded bases. Margins are finely serrated with mostly simple serration. There are glands of a medium grayed-red, near 181A, at the tip of each serrate. The upper surfaces are glossy and glabrous with the main and primary lateral veins noticeably recessed and secondary lateral veins barely recessed. The undersides are matte with the main vein protruding and only the primary lateral veins protruding to a small degree.

The length of mature leaves of the observed plants was 3 7/8- to 4 1/2-inches when measured from stem to tip along the rachis. The terminal leaflets are about 1 1/2- to 1 15/16-inches long and 7/8- to 1-inch wide at the widest point.

The upper surface of mature foliage is a very dark yellow-green, near 147A. The undersurface is near 147B and the color of the central vein is much lighter, near 145A. The upper surface of the new foliage is a medium green, between 144A and 137A. The under surface of new foliage is between 143C and 146C with some flushing of a color between 181A and 183C, heaviest toward the margins. The main vein is lighter, near 145C.

PETIOLES vary in length from 1 1/8- to 1 1/2-inches on the five-leaflet leaf and from 7/16- to 12/16-inch on the seven-leaflet leaf. The length of the RACHIS on the five-leaflet leaf is about 13/16-inch and on the seven-leaflet leaf it varies from 7/16- to 12/16-inch. The diameter of the petiole/rachis is about 1/16-inch. The adaxial surface is moderately grooved with hairs in the groove and hairs and stipitate glands along and near the ridges. The quantity of hairs and glands differs on each leaf from very few to a moderate amount. The color along the ridges is the same as that of the leaflet blades while the color in the groove is lighter, between 145B and 144D. The color of the abaxial surface is between 145B and 144D. There are hairs and stipitate glands randomly located on the surface along with a prickle located at or near the juncture with the leaflets.

PETIOLULES are the same as the rachis except the abaxial surface is the same lighter color and same texture as that of the main vein of the abaxial leaflet surface, near 145C. The petiolule to the terminal leaflet usually has 1 or 2 soft prickles. Petiolules to the terminal leaflets on five-leaflet leaves were measured at 21/32- to 24/32-inch long. Petiolules to the terminal leaflets on seven-leaflet leaves were measured at 20/32- to 22/32-inch in length.

STIPULES are attached in even pairs to each side of the petiole. On mature leaves they measure about 9/32-inch attached to the petiole, regardless of the size of the leaf, and 1/8-inch angled outward at about a forty degree angle from the petiole. The color of the adaxial surface is near 145C and the abaxial surface is near 139D. The part that is angled outward is the same color as the corresponding leaf surface. Margins appear loosely dentate with stipitate glands.

Growth:

The plant has a columnar and spreading growing habit with full branching and very vigorous growth. Canes are about 5 to 8 feet in height and of medium caliper for the class. Flowering stems were found to be 10 3/4- to 13 11/32-inches long, depending on how far down on the plant they originate.

The new wood is a medium yellow-green, near 144A. Old wood is a darker green, between 137A and 143A. Old wood may be almost entirely covered with grayed-brown lenticels of near 199B.

Prickles are straight and quickly narrow to acicular. They vary in length from 1/16- to 1/4-inch. Their base is elliptical or oval and on secondary laterals is narrow-oval. The length of the base varies from 2/32- to 7/32-inch. Quantities on the major canes vary between 1 and 4 per inch of stem. On laterals, they may be clustered, averaging between 7 and 11 per inch of stem. The color on the major stems is a medium yellowed-brown, between 164B and 199B. On the underside of the rachis/petiole their color is a much lighter, muted green-yellow, near 162D.

The plant displays an above average degree of resistance to powdery mildew and rust as compared to other commercial varieties grown under comparable conditions in Upland and Arroyo Grande, Calif. It is showing good resistance to black spot in early testing. The plant has been tested hardy in USDA zones 5 through 10.

It is claimed:

1. A new and distinct variety of miniature rose plant is claimed, substantially as described and illustrated herein, with vigorous columnar and spreading growing habit and producing flowers of a novel coloration.

* * * * *

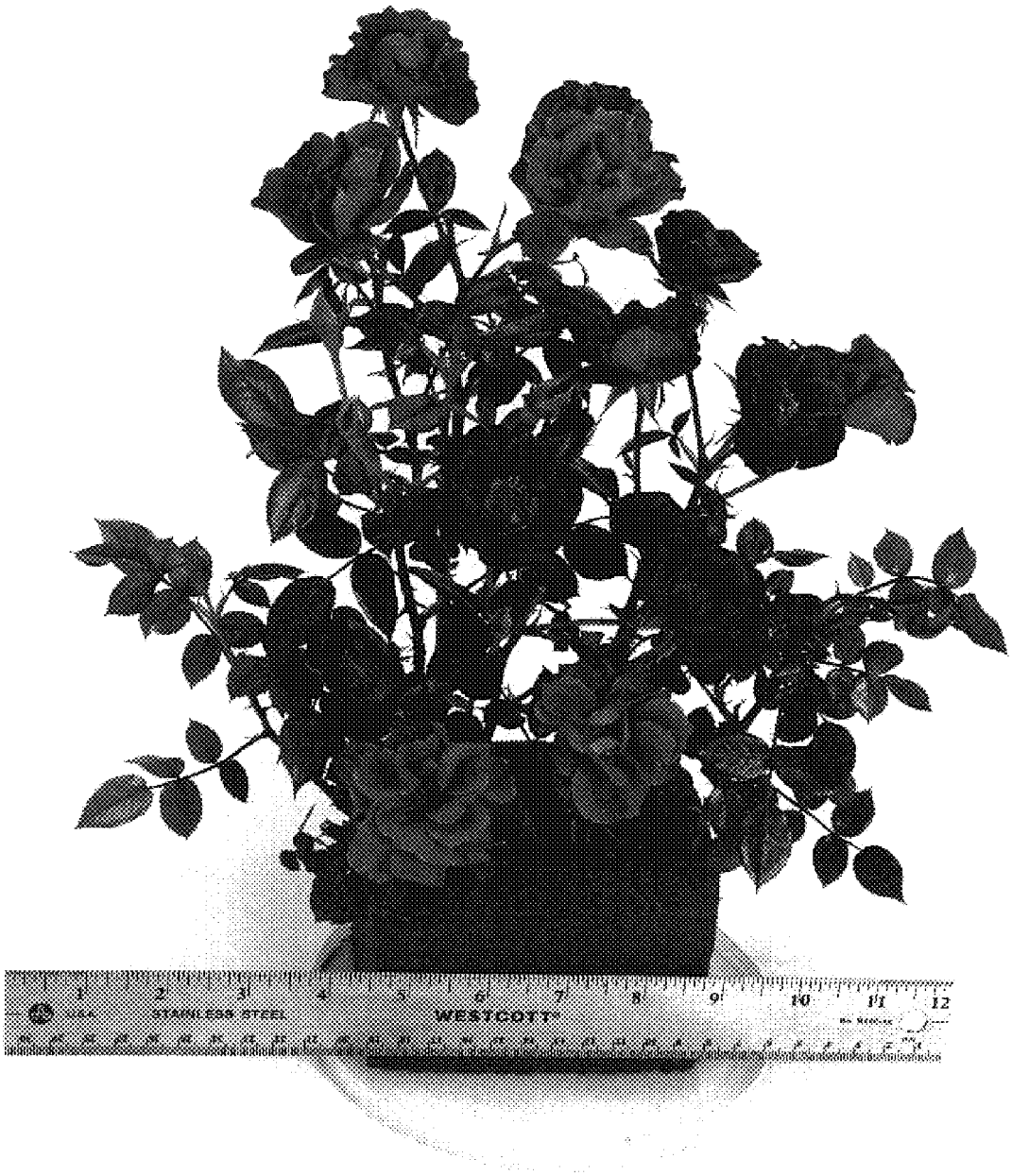
STAINLESS STEEL
WESTCOTT